(12) United States Patent
Zuegel

(10) Patent No.: US 9,435,710 B2
(45) Date of Patent: Sep. 6, 2016

(54) LINING TUBE AND METHOD FOR CHECKING THE CURING THROUGH OF A LINING TUBE OF RESIN-IMPREGNATED FIBER MATERIAL

(71) Applicant: BRANDENBURGER PATENTVERWERTUNG GBR, Landau (DE)

(72) Inventor: Frank Zuegel, Hemmingen (DE)

(73) Assignee: Brandenburger Patentverwertung GbR, Landau (DE)

( * ) Notice: Subject to any disclaimer, the term of this patent is extended or adjusted under 35 U.S.C. 154(b) by 517 days.

(21) Appl. No.: 13/952,820

(22) Filed: Jul. 29, 2013

(65) Prior Publication Data

US 2014/0030454 A1  Jan. 30, 2014

(30) Foreign Application Priority Data

Jul. 28, 2012 (DE) .................. 10 2012 014 997

(51) Int. Cl.

| | |
|---|---|
| *G01M 3/40* | (2006.01) |
| *F16L 55/165* | (2006.01) |
| *G01N 27/20* | (2006.01) |
| *B29C 35/10* | (2006.01) |
| *B29C 35/08* | (2006.01) |
| *E03F 3/06* | (2006.01) |

(52) U.S. Cl.
CPC ................ *G01M 3/40* (2013.01); *B29C 35/10* (2013.01); *F16L 55/1656* (2013.01); *G01N 27/20* (2013.01); *B29C 2035/0827* (2013.01); *E03F 2003/065* (2013.01); *Y10T 428/1334* (2015.01)

(58) Field of Classification Search
CPC ........... G01M 3/40; B29C 2035/0827; B29C 35/10; Y10T 428/1334; F16L 55/1656; G01N 27/20
See application file for complete search history.

(56) References Cited

U.S. PATENT DOCUMENTS 5,551,484 A * 9/1996 Charboneau ........ F16L 55/1656
138/104

* cited by examiner

*Primary Examiner* — Michael C Miggins
(74) *Attorney, Agent, or Firm* — Laurence A. Greenberg; Werner H. Stemer; Ralph E. Locher

(57) ABSTRACT

A lining tube of resin-impregnated curable fiber material, which after being pulled in and made to expand within a conduit, is cured from the inside by irradiating with electromagnetic radiation and/or heat. A device for checking the curing through of the fiber material contains a first and second electrical conductor, which extend parallel to one another over a length of the lining tube and arranged between which is a portion in strip form of a reaction resin that has a higher electrical conductivity in the liquid state than in the cured state of the same. A method checks the curing through of the lining tube for the final check on the complete curing through of the reaction resin, the electrical resistance is recorded at two adjacent ends of the first and second electrical conductors and after that the recorded resistance value is compared with a predetermined resistance setpoint value.

10 Claims, 4 Drawing Sheets

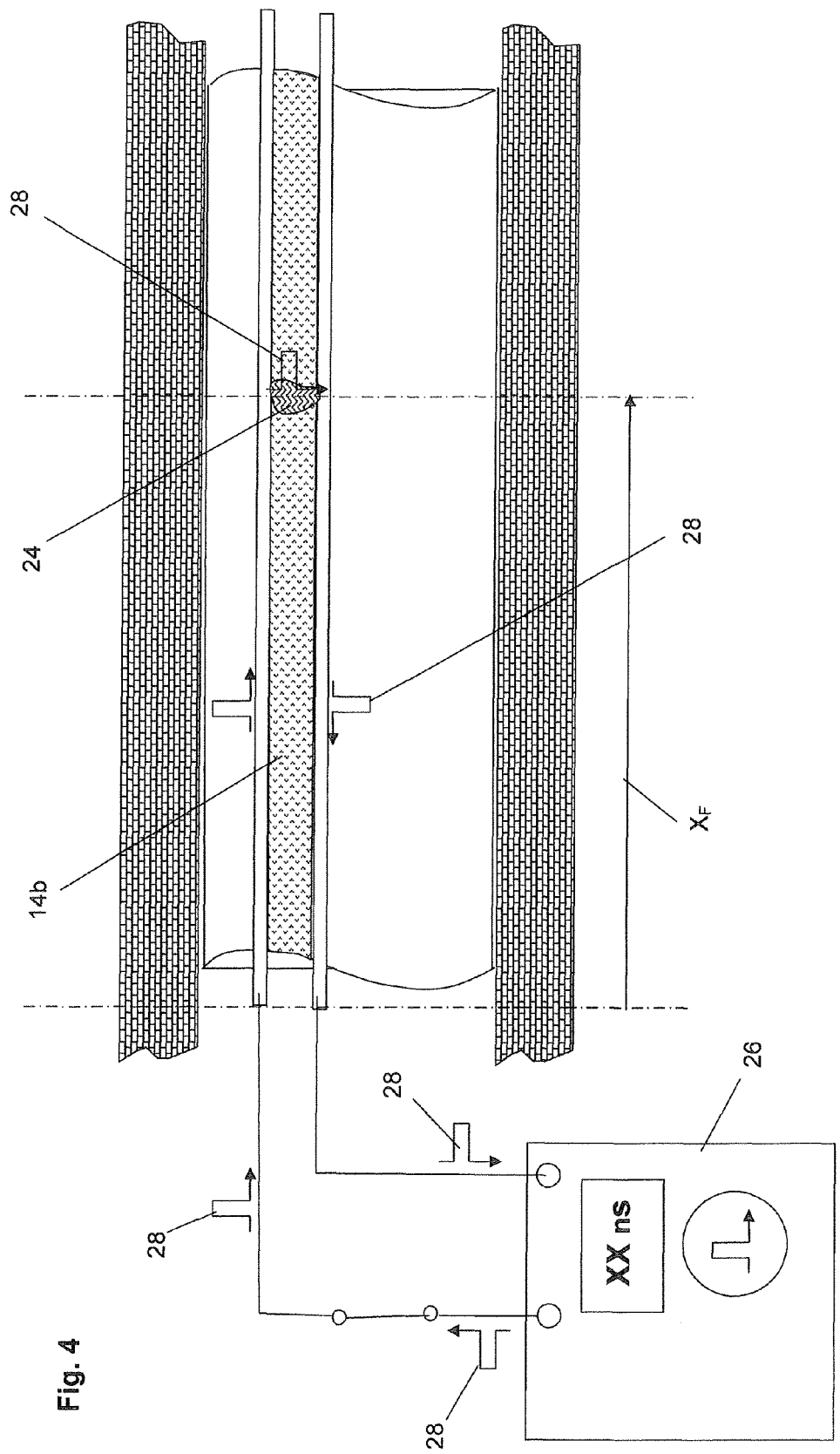

US 9,435,710 B2

LINING TUBE AND METHOD FOR CHECKING THE CURING THROUGH OF A LINING TUBE OF RESIN-IMPREGNATED FIBER MATERIAL

CROSS-REFERENCE TO RELATED APPLICATION

This application claims the priority, under 35 U.S.C. §119, of German application DE 10 2012 014 997.2, filed Jul. 28, 2012; the prior application is herewith incorporated by reference in its entirety.

BACKGROUND OF THE INVENTION

Field of the Invention

The invention relates to a lining tube of resin-impregnated curable fiber material, containing a device for checking the curing through of a fiber material and a method for checking the curing through of such a lining tube after being pulled into a conduit to be rehabilitated.

In the area of the trenchless rehabilitation of defective pipelines, such as for example defective sewers, use is increasingly being made of lining tubes which are referred to as "inliners" and are formed from a fiber material, in particular of glass fabric. The inliner is impregnated with a liquid reaction resin which is cured after the lining tube has been pulled into the pipeline and made to expand with the aid of compressed air by introducing hot steam or hot water or a light of a radiation source which is moved through the lining tube and irradiates the inner walls of the lining tube.

This involves the problem that the impermeability of the rehabilitated pipeline after the curing of the reaction resin depends very much on the curing operation being carried out properly, since even a single small portion in which the reaction resin is not cured through, or not cured through completely, is sufficient to produce a mechanical weakness of the form that external influences, such as for example the ground loads acting, cannot be withstood, or the inliner does not withstand internal influences, such as for example high-pressure flushing operations.

A further problem involved here is that the previously mentioned permeable locations, in which the reaction resin is not completely cured locally, for example due to an irradiating time that is too short or due to shadow effects, cannot be repaired subsequently, or only in a very laborious way. On account of the currently applicable strict official regulations for conduits rehabilitated by lining tubes, it is therefore often necessary in practice to remove the lining tubes again completely from the conduit, which entails very great effort and corresponding costs.

BRIEF SUMMARY OF THE INVENTION

It is accordingly an object of the present invention to provide a lining tube which, after being laid in a conduit and cured, provides the possibility of checking the complete curing through of the reaction resin. A further object of the invention is to provide a method by which the curing through of a lining tube pulled into a conduit to be rehabilitated can be checked during the curing operation and after completion of the same.

According to the invention, a lining tube containing one or more layers of fiber material which are impregnated with a reaction resin which is curable in a known way by heat or else electromagnetic radiation, in particular UV radiation. The fiber slivers are preferably applied here to an inner film tube, which is formed of a preferably styrene-impermeable plastics material, preferably a thermoplastic material. Although the ply or plies of fiber material can also be obtained by mats of fiber material being sewn together at the edges or laid lengthwise, in a radially overlapping manner, they are preferably obtained by fiber slivers being continuously wound around a winding mandrel, to which the continuous inner film tube has previously been applied. Once the lining tube according to the invention, with the reaction resin in the non-cured state, has been pulled into a conduit to be rehabilitated, the ends of the lining tube are closed and compressed air is applied to the tube, so that the layers of fiber material come to lie against the inner side of the conduit. This is followed by curing of the lining tube by introducing electromagnetic radiation, in particular UV radiation, or else heat, in particular hot steam or a heated liquid, into the interior space of the lining tube in order to cure the reaction resin. In order to ensure here that the reaction resin, or the fiber material, is completely cured through during and/or after the curing operation, the lining tube according to the invention preferably contains on its outer side a device with which the curing through of the fiber material can be checked.

According to the preferred embodiment of the invention, the device for checking the curing through of the fiber material contains a first and a second electrical conductor, in particular in the form of a first and a second conducting, electrically uninsulated wire or flat strip conductor, which extend substantially parallel to one another over the length of the lining tube.

Arranged between the two electrical conductors, which preferably run parallel to one another over their entire length, is a portion in strip form of reaction resin that has a higher electrical conductivity in the liquid state than in the cured state. Here, the reaction resin in the portion in strip form forms an electrical conducting connection over the entire length of the two conductors, by way of which the electrical current can flow from one conductor to the other conductor when the ends of the conductors are connected to a power source or an electrical signal generator.

In the case of the preferred embodiment of the invention, preferably only the reaction resin in the portion in strip form, but not the reaction resin in the fiber material that forms the wall of the lining tube, contains electrical charge carriers in the form of one or more salts, which are mixed in with the reaction resin, for example by stirring, and are homogeneously contained in it. In order to create substantially the same curing conditions here, the reaction resin into which the salt is introduced is preferably identical to the resin with which the fiber material is impregnated.

Although in principle almost any organic or inorganic salt that breaks down into positive and negative charge carriers in aqueous solution is suitable as the substance that reduces the conductivity of the reaction resin in the portion in strip form before the curing of the resin and increases it by a multiple value in comparison after the curing, a salt of ammonia and/or a salt of potassium or sodium is preferably used. A suitable salt is, for example, tetraalkyl ammonium methylsulfate, which is mixed in with the reaction resin containing a photoinitiator, preferably UP resin, in an amount of 0.5 to 10% by weight, preferably in the range from 1 to 4% by weight and particularly preferably 3% by weight, in each case with respect to the total weight of the mixture, by stirring.

Depending on the temperatures, the air humidity and other ambient conditions, it is similarly possible to obtain the desired properties of the resin by using a mixture of two or more of the salts mentioned in order to increase the conductivity of the resin in the liquid state, and thereby bring the properties of the reaction resin, in particular the curing behavior, closer to the properties of the resin in the fiber material of the lining tube.

Thus, for example, by mixing 3% by weight of tetraalkyl ammonium methylsulfate with a known UP resin, which contained a UV initiator, it was possible to obtain a resin mixture which, in the liquid state, produced an ohmic resistance in the range of initially 12 megaohms at two conductors of copper wire, with a length of 0.4 m, that were arranged at a distance of about 1 cm from one another. After irradiating the specimen using a UV vapor lamp, it was initially possible to observe a reduction in the ohmic resistance to about 200 kohms, before the ohmic resistance then rose again sharply after an irradiating time of about 4 minutes and, after about 10 minutes, reached the end of the measuring range of the measuring instrument, which ends at 220 megaohms.

According to a further concept on which the invention is based, arranged between the first and second electrical conductors is a carrier medium receiving the liquid reaction resin, in particular a polyester nonwoven or glass-fiber nonwoven, which absorbs and binds the resin. This produces the advantage that the liquid reaction resin with the mixed-in charge carriers, or the salts dissolved therein, does not run off from the electrical conductors, in spite of the liquid state, when the lining tube is brought into a lateral position, in which one electrical conductor is arranged in an upper position and the other electrical conductor is arranged in a position lying thereunder, before being pulled into the conduit to be rehabilitated or during transportation over a relatively long period of time. In such a case, running down of the resin is effectively prevented on account of the binding of the reaction resin to the nonwoven.

In the case of the preferred embodiment of the lining tube, the first and second electrical conductors are preferably arranged lying parallel next to one another on the outer side of the lining tube, as seen in the longitudinal direction of the lining tube. Although the distance between the two conductors may also be kept comparatively small, for example 0.5 of a centimeter, the distance in the case of the preferred embodiment is preferably 1 cm or more, in order that, when there is a variation in the distance between the two conductors, there are no excessive fluctuations of the measured resistance in dependence on the respective position on the conductor, which is referred to hereinafter as the X position. This allows the curing operation to be monitored, for example by a continuous measurement of the momentary resistance at one end of the two electrical conductors, and early detection and correction of an error, for example excessive speed of the radiation source.

According to a further embodiment of the invention, the first and second electrical conductors may be arranged on diametrically opposite sides of the lining tube, in the region of the outer circumferential surface, whereby it is made possible in principle to check the curing of the reaction resin over the entire circumference of the lining tube. Although the two conductors are in this case preferably embedded in a nonwoven that surrounds the entire circumference of the lining tube, there is likewise the possibility of impregnating the last fiber sliver layer applied to the outer side of the lining tube with the conducting reaction resin and subsequently laying the two electrical conductors onto the upper side and underside of the fiber tube, in a way similar to a longitudinal tensioning band, before the fiber tube is surrounded with an outer film tube.

According to a further embodiment of the invention, it may also be provided that two or more pairs of first and second electrical conductors and regions in strip form of nonwoven material arranged between them are arranged around the circumference of the lining tube at preferably equal intervals, for example with a relative angular offset of 120°, 90° or 60° etc., in order to check the complete curing of the reaction resin after irradiation of the fiber material from the inside at a number of points of the circumference. This produces the advantage that the complete curing through of the reaction resin can be checked with a high degree of reliability even in the region of bends of a conduit to be rehabilitated, in which differences in the irradiating time and intensity often occur in the case of curing by UV light. These differences are caused, for example, by the wall length being greater on the outer side of the bend than on the inner side. Moreover, in such regions shadows are often cast, among the effects of which are an uneven irradiation intensity and resultant uneven curing.

Furthermore, it may be provided that the region in strip form with the two electrical conductors extends helically around the outer side of the fiber material. With only one pair of electrical conductors, this allows early detection of unevennesses in the curing that are attributable in particular to a differing spatial radiation distribution of the UV light of a light source that is passed through the lining tube for curing the reaction resin. This provides the possibility of readjusting the UV lamps or other components of the radiation source at an early time, before the defective radiation source is pulled completely through the conduit to be rehabilitated, and subsequently has to be pulled through again in order to obtain complete curing through.

According to a further concept on which the invention is based, in the case of the method according to the invention for checking the curing through of a previously described lining tube, for the final check on the complete curing through of the reaction resin after the curing of the same, the electrical resistance is recorded at two adjacent ends of the first and second electrical conductors. A known conventional ohmmeter may be used for this, the inputs of which merely have to be connected for this purpose to the two end portions of the first and second electrical conductors at one end of the lining tube. If the ohmic resistance, measured before the curing at only a few megaohms, after completion of the curing operation lies above the value that can be measured with a conventional ohmmeter, for example 500 megaohms, this is evidence that the lining tube is completely cured through.

In order to additionally ensure here that a rupture of one of the two electrical conductors has not occurred during the curing operation, the end portions of the two electrical conductors lying opposite from the end portions that are used for the measurement, at the other end of the lining tube, may be short-circuited before carrying out the measurements. By recording the internal resistance of the two electrical conductors short-circuited at one end before the beginning of the curing of the reaction resin, the total internal resistance of the first and second conductors connected in series can be recorded with a commercially available measuring instrument, which in the case of preferably used conductors of copper wire or of constantan wire lies around several orders of magnitude above the value of the ohmic resistance that is obtained with the conductor ends open, on account of the resistance of the electrically conducting reaction resin. This allows systematic measuring errors to be avoided in an easy way, even when using untrained personnel, by simple measures, in that before and after the curing operation the ohmic resistance between the open and short-circuited conductors is measured and logged.

According to a further concept on which the invention is based, during the curing of the reaction resin by a radiation source, in particular a UV radiation source, that is moved through the interior space of the lining tube in a known way at a predetermined speed, the speed is changed in dependence on the momentarily recorded value of the resistance and is preferably controlled. This makes use of the fact recognized by the applicant that the ohmic resistance of the conducting reaction resin is initially reduced by the irradiation of UV light before it rises again. Using this recognition, the speed of movement of the radiation source is preferably changed such that this minimal resistance value is kept substantially constant during the entire curing operation. If, at the beginning of the curing operation, the radiation source is pulled through the lining tube at a comparatively low speed, which lies below the optimum speed, there occurs a value for the momentary resistance measured that is initially too high. By gradually increasing the pulling-through speed, the continuously measured value for the ohmic resistance is then reduced until such time as it rises again. Variation of the pulling-through speed about the minimal value, determined in this way, for the continuously measured ohmic resistance allows the pulling-through speed of the radiation source to be set to the minimal value with minor deviations.

According to a further concept on which the invention is based, after the completion of a curing operation or else during the curing operation, the position of a region in which the reaction resin is not completely cured through within the lining tube is determined by a series of electrical voltage pulses being applied to the first and second electrical conductors, preferably at the adjacent ends of the conductors, by way of an electrical signal source, and the transit time of the pulses is recorded. This allows the position—which is referred to hereinafter as the X position—at which the not completely cured-through region is arranged in the lining tube to be determined by the transit time of a voltage pulse with the speed of propagation $C_{signal}$ of the electrical pulses along the two electrical conductors and the corresponding conducting region between the conductors being multiplied and the result divided by two. The speed of propagation of the electrical pulses, which may, for example, be square-wave pulses, is preferably determined here in advance by a comparative measurement on a sample lining tube. It goes without saying that, to increase the measuring accuracy of the average transit time of the signals, it is also possible to perform a number of successive measurements with identical or different signals, from which a mean value for the average transit time is then calculated. Once the X position of the region has been determined in the way previously described, the radiation source is moved to this X position and the inner side of the lining tube is irradiated once again in the region of this position. The ohmic resistance between the two conductor ends also in this case being continuously measured, in order to verify on the basis of a rising measured value for the ohmic resistance that the correct X position has been determined. Similarly, when the predetermined resistance setpoint value or end value is achieved, for example 300 megaohms, the radiation source is switched off, in order to prevent overheating of the inner wall of the lining tube, in particular of the inner film tube arranged on the latter.

It goes without saying that, in the case of reaction resin that is not cured by UV light, but for example by heat or some other electromagnetic radiation, the local post-curing of the reaction resin takes place by introducing the corresponding electromagnetic radiation and/or heat, here too the ohmic electrical resistance at the adjacent ends of the two electrical conductors being continuously recorded during the post-curing, and the post-curing being ended when the predetermined resistance setpoint value, which is for example 300 megaohms, has been reached.

Other features which are considered as characteristic for the invention are set forth in the appended claims.

Although the invention is illustrated and described herein as embodied in a lining tube and a method for checking the curing through of a lining tube of resin-impregnated fiber material, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

BRIEF DESCRIPTION OF THE SEVERAL VIEWS OF THE DRAWING

FIG. 3 is a schematic representation of the lining tube with a defect, at which the conducting reaction resin is not completely cured through; and FIG. 4 is a schematic representation of the lining tube from FIGS. 1 to 3, during the localizing of the defect with the aid of a signal generator connected to the two conductor ends.

DESCRIPTION OF THE INVENTION

Figure 1:
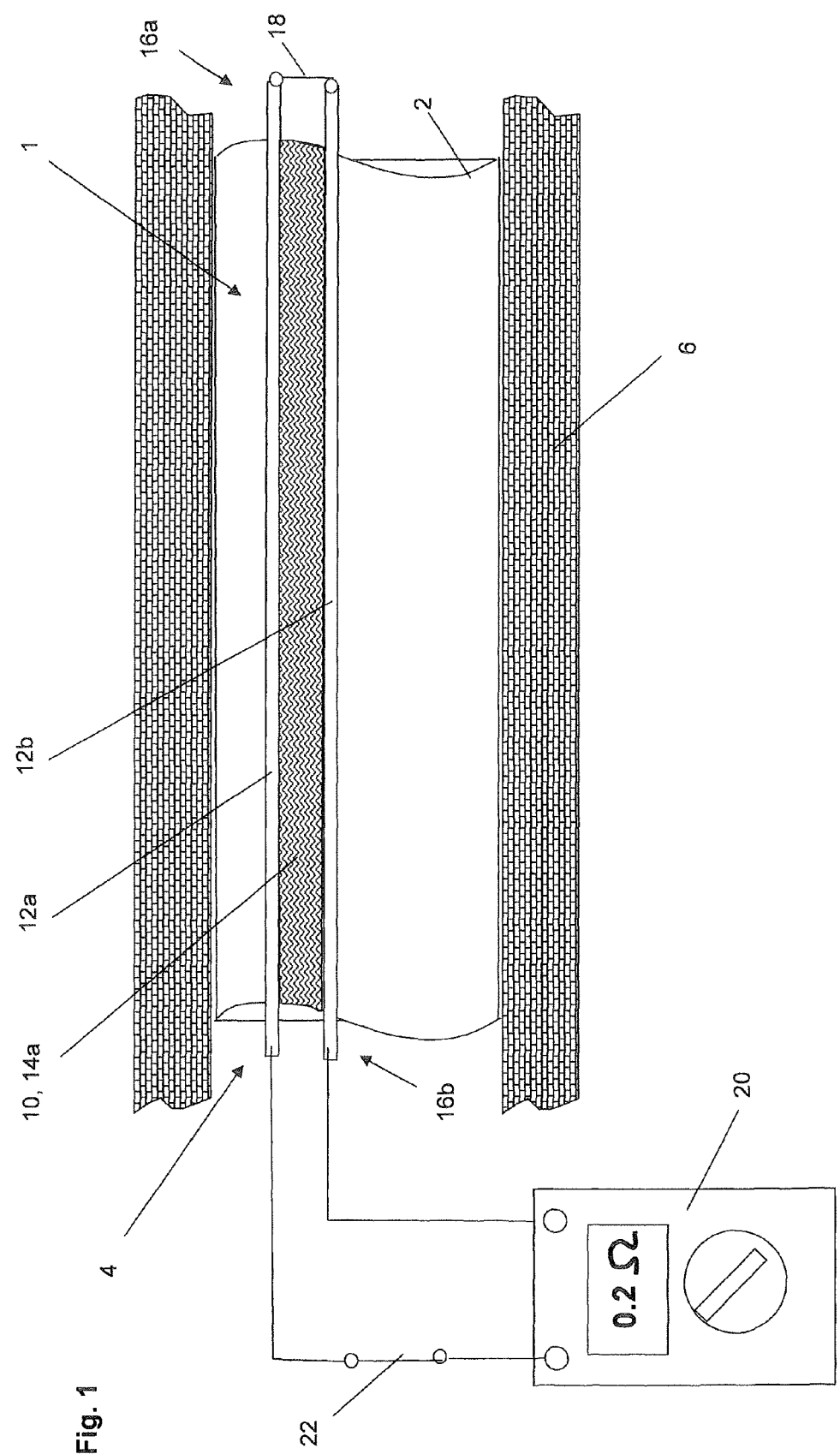
FIG. 1 is a schematic representation of a conduit with a pulled-in lining tube, arranged on an outer side of which is a nonwoven strip impregnated with conducting reaction resin, with a first and a second electrical conductor, which are short-circuited at one end in order to determine a total resistance before a beginning of a curing operation according to the invention.

Referring now to the figures of the drawing in detail and first, particularly, to FIG. 1 thereof, there is shown a lining tube 1 according to the invention formed of a fiber material 2, which is impregnated with a reaction resin that is not shown any more specifically for representational reasons. A device 4 is shown with which a curing through of the fiber material 2 can be checked after the lining tube 1 has been pulled into a conduit 6 to be rehabilitated, the same has been made to expand by compressed air and the reaction resin has been cured with the aid of a radiation source 8. For this purpose, the device 4 contains a portion in strip form 10, which is formed of a nonwoven material which is arranged on the outer side of the lining tube 1 and extends over the entire length of the same. Arranged laterally of the portion in strip form 10, or else overlapping with the nonwoven material, are a first electrical conductor 12*a* and a second electrical conductor 12*b*, preferably of nickel wire, which respectively have a width of, for example, 5 mm and a height of, for example, 2 mm. The two electrical conductors 12*a* and 12*b*, which may also be formed of different materials, for example copper and nickel or some other suitable metal alloy, are embedded in the nonwoven material parallel to one another preferably at a distance of, for example, 1 cm and accordingly bound between their longitudinal edges the portion in strip form 10. The nonwoven material is impregnated with an electrically conducting liquid reaction resin 14a, which is likewise in electrical contact with the two conductors 12a, 12b. The reaction resin is preferably the same reaction resin as the resin with which the fiber material 2 is impregnated. In order to provide the electrical conductivity of the normally non-conducting reaction resin, mixed in with the liquid resin are electrical charge carriers in the form of a salt, which is preferably a salt of ammonia, which is contained in the reaction resin in an amount of preferably about 3% by weight, with respect to the weight of the finished mixture.

As can be seen here in detail in the representation of FIG. 1, after the lining tube 1 has been pulled into the conduit 6 to be rehabilitated the two electrical conductors 12a, 12b are short-circuited at one end 16a of the lining tube 1 by way of an electrically conducting connection 18, for example a terminal, and the total resistance of the short-circuited conductors 12a, 12b is measured at the other end 16b, in order to ensure that the two electrical conductors are operating correctly, and in particular are not ruptured. The measuring of the ohmic resistance at the second end 16b of the lining tube 1 is performed in this case with the aid of a known commercially available measuring instrument 20, which has a measuring range of, for example, 1 ohm to 220 megaohms, or greater. In the representations, the electrical connection of the measuring instrument 20 is indicated by a switch 22, which although provided in practice is not absolutely necessary when a simple resistance measuring instrument is used.

Figure 2:
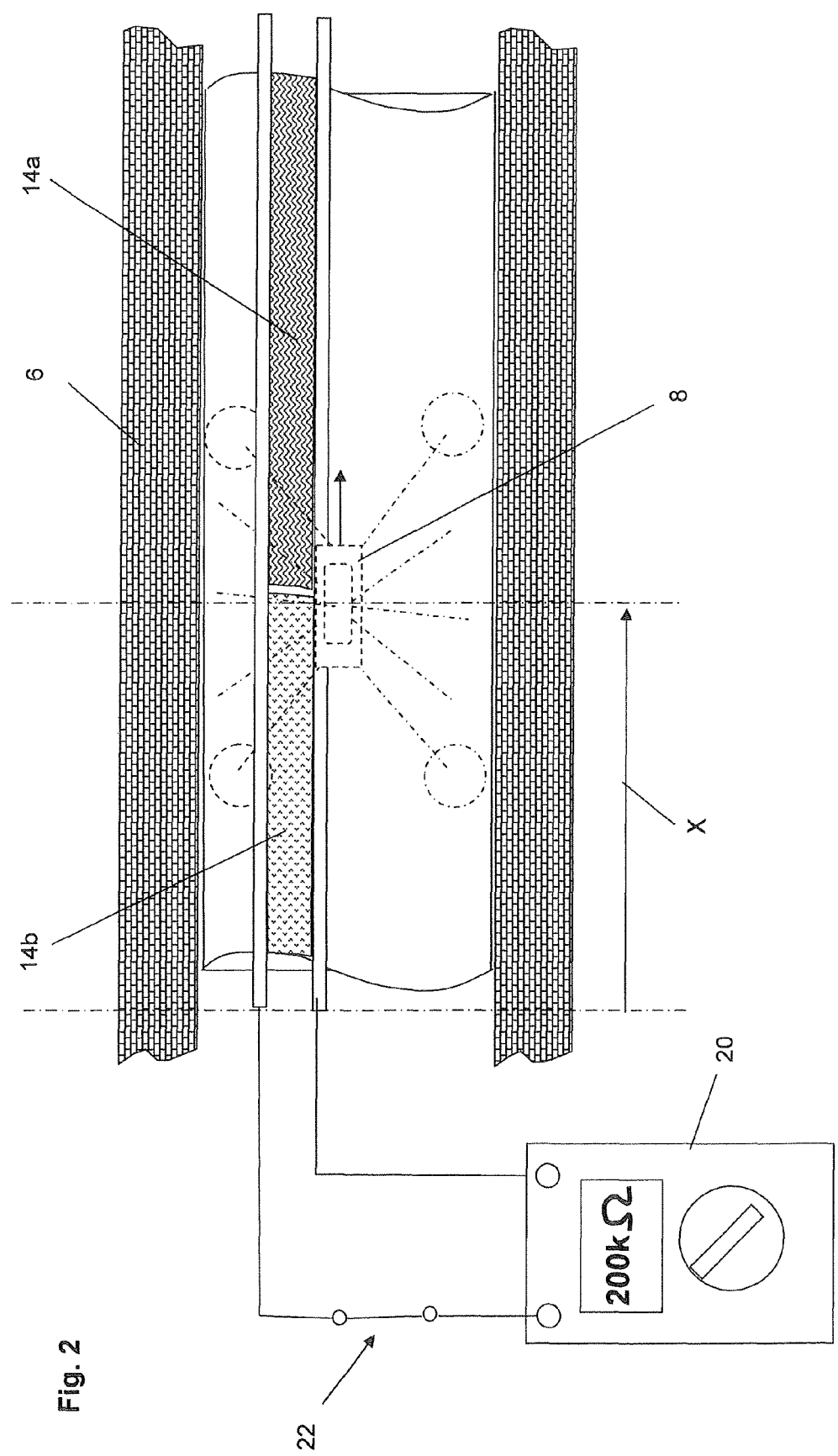
FIG. 2 is a schematic representation of the lining tube during a curing operation when pulling through an indicated UV radiation source, which is located at an X position in the conduit.

As shown in FIG. 2, after the lining tube 1 has been pulled into the conduit and made to expand, the radiation source 8 is moved through the interior space of the conduit, by way of a pulling cable that is not shown any more specifically, and the inner surface of the lining tube 1 lying against the inner wall of the conduit is irradiated with UV light, which penetrates through the fiber material 2 of the lining tube from the inside and after that impinges from below on the portion in strip form 10. The UV light interacts in a known way with UV initiators in the liquid reaction resin of the fiber material 2 and also the liquid conducting reaction resin 14a in the portion in strip form 10, which thereby break down into radicals and initiate a polymerization of the respective resin.

When the radiation source 8 with a predetermined light intensity is moved through the lining tube 1 at a predetermined speed, for example 1.5 m/min, this generally leads to complete curing through of the reaction resin, which is indicated by the different shadings of the portion in strip form 10 in FIG. 2. Thus, up to the position X of the radiation source 8, the reaction resin 14b is already cured through completely and, as a result, has lost its electrical conductivity, since the electrical charge carriers can no longer move freely in the resin; by contrast, beyond the position X, the reaction resin 14a is still liquid and has its original conductivity.

Once the radiation source 8 has been pulled completely through the lining tube 1, and the resin has cured, the ohmic resistance at the two ends of the conductors 12a, 12b is finally recorded with the measuring instrument 20. If the measured ohmic resistance of the conductors 12a, 12b, which are not otherwise electrically connected to one another, lies above a predetermined resistance setpoint value, for example 200 megaohms, complete curing through of the conducting liquid reaction resin 14a in the nonwoven material of the portion in strip form 10 can be assumed, which in turn means that the reaction resin in the fiber material 2 lying thereunder, which is identical in terms of its basic composition, is also cured through completely.

Figure 3:
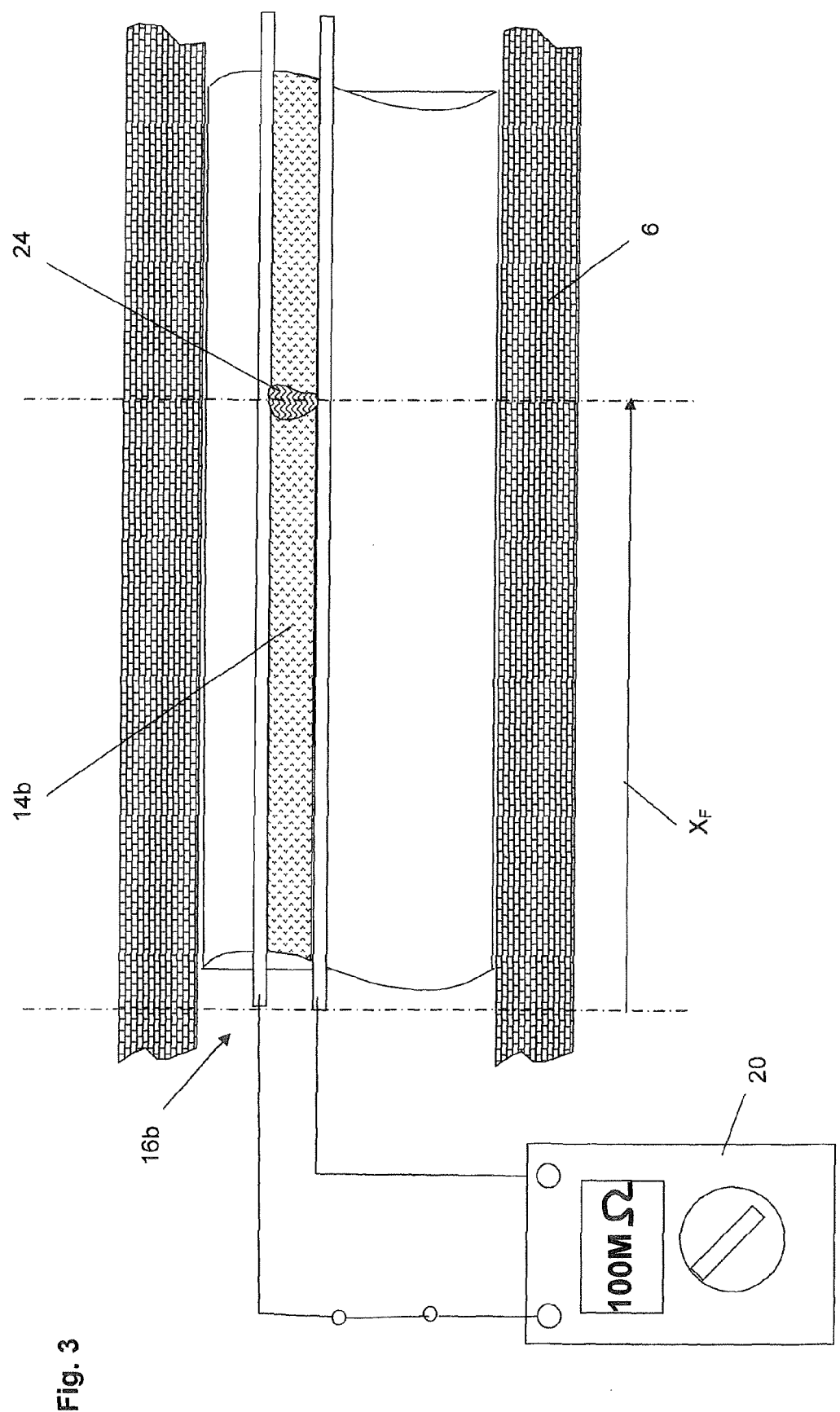

If, on the other hand, on account of an irradiating time that is too short or some other problem, there is a region in the portion in strip form 10 in which the liquid conducting reaction resin 14a is not yet cured through completely, referred to hereinafter as a defect 24, this produces an electrically conducting connection between the two conductors 12a and 12b. This defect 24, situated at a distance from the ends of the conductors 12a, 12b, has the effect that the predetermined resistance setpoint value is not reached, but instead a significantly lower ohmic resistance is measured, indicated by way of example on the measuring instrument 20 in FIG. 3 as 100 megaohms.

In order to determine the position in which the defect 24 is located, the two ends of the conductors 12a, 12b are connected to an electrical signal source 26, which applies to the one electrical conductor 12a at least one electrical voltage or current pulse 28, which returns to the signal source 26 by way of the defect 24 and the second electrical conductor 12b. By measuring the transit time that an electrical voltage or current pulse 28 needs from the signal source 26 to the defect 24 and back, a distance $X_F$ between the signal source 26 and the defect 24—which for the sake of simplicity is equated hereinafter to half the distance of the defect 24 from the second end 16b of the lining tube 1—can then be calculated. For this purpose, the measured transit time is multiplied by half the value of the speed of propagation of the electrical pulses 28, which has preferably been determined beforehand by a comparative measurement on a specimen of the portion in strip form 10. It goes without saying that the position $X_F$ of the defect 24 can be determined with a high degree of accuracy by account being taken of the length of the signal leads, and multiplication by preferably empirically determined correction factors, which take into account, for example, the pulse length, pulse frequency, the length of the lining tube, the temperature of the same and also the composition of the reaction resin, etc.

Once the approximate position $X_F$ of the defect 24 has been determined, the radiation source 8 is moved into the region of this approximate position $X_F$ and the inner wall of the lining tube 1 is irradiated once again. Here it is of advantage if, during the renewed irradiation, the ohmic resistance at the two ends of the conductors is measured continuously, in order on the one hand to detect whether the correct position of the defect 24 has been determined, and on the other hand to ensure that the re-irradiating operation is ended in good time when the predetermined resistance setpoint value has been reached. This allows the re-irradiating time to be reduced considerably, which also reduces the risk of an inner film tube that is likewise preferably contained inside the lining tube, and seals the fiber material 2 on the inner side of the lining tube against the escape of substances from the reaction resin, overheating or being damaged.

The invention claimed is:

1. A lining tube of a resin-impregnated curable fiber material, the lining tube after being pulled in and made to expand within a conduit can be cured from an inside by irradiating with at least one of electromagnetic radiation heat, the lining tube comprising:
   a device for checking a curing through of the resin-impregnated curable fiber material, said device having a first and a second electrical conductor extending substantially parallel to one another over a length of the lining tube; and a portion in strip form disposed between said first and second electrical conductor, said portion in strip form formed of a reaction resin having a higher electrical conductivity in a liquid state than in a cured state of said reaction resin.

2. The lining tube according to claim 1, wherein said first and second electrical conductors are disposed lying next to one another on an outer side of the lining tube.

3. The lining tube according to claim 1, wherein said first and second electrical conductors are disposed on diametrically opposite sides of the lining tube, in a region of an outer circumferential surface.

4. The lining tube according to claim 1, wherein:

said first and second electrical conductors are one of at least two pairs of first and second electrical conductors; and said portion in strip form is one of at least two portions in strip form disposed between said pairs and disposed around a circumference of the lining tube at equal intervals.

5. The lining tube according to claim 1, wherein said portion in strip form with said first and second electrical conductors extend helically around an outer side of said resin-impregnated curable fiber material.

6. The lining tube according to claim 1, wherein said first and second electrical conductors are disposed lying next to one another on an outer side of the lining tube as seen in a longitudinal direction of the lining tube.

7. The lining tube according to claim 1, wherein said reaction resin in said portion in strip form contains electrical charge carriers in a form of at least one salt distributed substantially homogeneously in said portion.

8. The lining tube according to claim 7, wherein said reaction resin in said portion in strip form contains at least one of sodium chloride, sodium fluoride, a salt of ammonia, potassium chloride, potassium fluoride, an organic salt or a mixture of the aforementioned salts.

9. The lining tube according to claim 1, further comprising a carrier medium disposed between said first and second electrical conductors, said carrier medium receiving said liquid reaction resin.

10. The lining tube according to claim 9, wherein said carrier medium is one of a polyester nonwoven or a glass-fiber nonwoven.

* * * * *